US005763618A

United States Patent [19]

Watanabe et al.

[11] Patent Number: 5,763,618
[45] Date of Patent: Jun. 9, 1998

[54] MANUFACTURING METHOD OF SULFIDES

[75] Inventors: Ryuzou Watanabe; Shinri Tanaka; Katsuji Ota; Michiko Nagato; Tomio Horiuchi, all of Hino, Japan

[73] Assignee: Konica Corporation, Japan

[21] Appl. No.: 639,767

[22] Filed: Apr. 29, 1996

[30] Foreign Application Priority Data

May 12, 1995 [JP] Japan ................................. 7-114600
Aug. 25, 1995 [JP] Japan ................................. 7-217435
Oct. 18, 1995 [JP] Japan ................................. 7-270199

[51] Int. Cl.$^6$ ................................................. C07D 257/04
[52] U.S. Cl. ................... 548/144; 548/366.4; 548/252; 548/360.5; 544/114; 560/18; 558/391
[58] Field of Search ...................... 548/366.4, 252, 548/360.5, 144; 544/114; 560/18; 558/391

[56] References Cited

U.S. PATENT DOCUMENTS 5,405,969 4/1995 Wright et al. .

OTHER PUBLICATIONS

Bulletin of Chemical Society of Japan, vol., 51, No. 10, 1978(3 pgs.) Journal of Chemical Society, Perkin Transactions 1, 1977, (4 pgs).

*Primary Examiner*—Samuel Barts
*Attorney, Agent, or Firm*—Jordan B. Bierman; Bierman, Muserlian and Lucas

[57] ABSTRACT

A method of manufacturing a sulfide comprises the steps of (a) dissolving a thiol in a solvent to form a solution; (b) oxidizing the thiol to a disulfide in the presence of a first oxidizing agent in the solution; (c) reacting the disulfide with a coupler in the presence of a base and a second oxidizing agent, without isolation of said disulfide from the solution, to form a reaction mixture in which the sulfide is produced; and (d) obtaining said sulfide.

22 Claims, No Drawings

MANUFACTURING METHOD OF SULFIDES

FIELD OF THE INVENTION

The present invention relates to a manufacturing method of sulfides, and particularly to a method of manufacturing sulfides at low cost, but with high yield and excellent workability.

BACKGROUND OF THE INVENTION

Descriptions regarding reactions of carbanion with disulfides are provided in several literature. For example, there is a description in Bull. Chem. Soc. JPN., 51, 3008 (1978) in which β-ketoester is reacted with aryldisulfide in the presence of potassium iodide in HPMA. Since this method employs a dry, purified HPMA as a reaction solvent, it is difficult to mass produce industrially and economically an objective product. This method gives low yield, which is unsatisfactory. Further, only one half of the disulfide chemical structure is used as a releasing group, and one mole of the arylsulfide is necessary for one mole of the β-ketoester, which is not economically feasible.

There is, in Japanese Patent O.P.I. Publication No. 51-16924/1976, a description of a method that disulfide is reacted with carbanion in the presence of an alkali to synthesize sulfide. This method requires the disulfide of the same mole as the carbanion, since the thiolate anion produced during the reaction is not oxidized to the disulfide by an oxidizing agent, and therefore, it is difficult to produce the sulfide effectively and economically.

There is also a description of reactions of carbanion, adjacent to phosphineoxide, with disulfide in J. Chem. Soc., Perkin Trans I, 2263 (1977). Since this method employs an expensive, dangerous organic metal reagent and an expensive solvent, tetramethylethyleneamine, and the reaction is carried out at −78° C. under anhydrous condition, this method is also difficult to mass produce industrially and economically an objective product.

There is also in U.S. Pat. No. 5,405,969, a description of a method that thiol or disulfide is reacted with carbanion in the presence of a base or an oxidizing agent to synthesize sulfide. In this method, it is relatively easy to convert thiol or disulfide to sulfide. However, there are some problems in the industrial practice of this method.

A first problem is one in synthesizing thiol or disulfide as a starting material. Disulfide (2), which is described in Synthetic Examples 2 and 3 of the U.S. Pat. No. above, is generally synthesized through 2,2'-dithiodianiline (1), but this compound has strong stimulation and causes eruptions on the skin. The other analogous disulfides have a similar tendency, and are therefore difficult to handle.

Reaction Formula 1

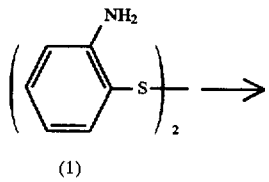

(1)

-continued
Reaction Formula 1

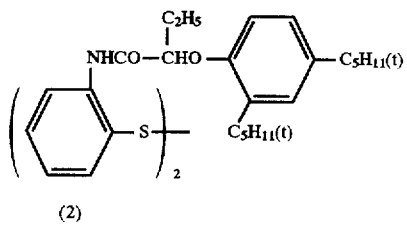

(2)

The following Reaction Formula 2 is considered in order to synthesize disulfide (2) without not through 2,2'-dithiodianiline (1). In this method, the acylation reaction rate from thiol (3) to thiol (4) is low, which is industrially disadvantageous.

Reaction Formula 2

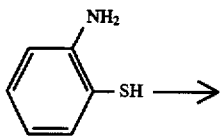

(3)

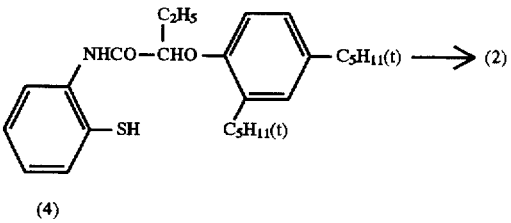

(4)

There is also a proposal in the specification of the above patent that thiol is oxidized to disulfide which is used for synthesis of sulfide. This method is easily conceived, since thiol is easily oxidized to disulfide, and in the synthesis of the sulfide, a reaction (Reaction Formula 3) is essential which comprises oxidizing thiol, which has been produced with sulfide on reaction of disulfide with carbanion, to disulfide.

In the synthetic reaction of sulfides, disulfide and thiol are consumed while the chemical reaction proceeds clockwise in the loop of the following Reaction Formula 3. In this reaction, there is no substantial difference between disulfide and thiol (equivalent to SR$^-$ in the presence of a base) as a starting material.

Reaction Formula 3

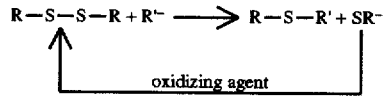

A second problem is that it is difficult to use in combination an oxidizing agent such as hydrogen peroxide and a solvent having a high solubilizing ability such as DMF, which are inexpensive, available and industrially advantageous.

In a chemical reaction it is desirable to sufficiently dissolve the reaction components in the solvent. However, most sulfides, which are compounds for manufacturing photographic agents, medicines, agricultural medicines or dyes, and most carbanions to be reacted with said sulfides are difficult to dissolve in an organic solvent. Therefore, use of a solvent having high solubilizing ability such as DMF is desirable. Two of the three synthetic examples, described in the specification of the above patent, employ DMF.

When DMF and hydrogen peroxide are used in combination, the hydrogen peroxide wastefully reacts with DMF and a dangerous oxidation product of DMF is produced.

In order to overcome these problems, all three synthetic examples described in the specification of the above patent employ N-methylmorpholino-N-oxide as an oxidizing agent. However, this oxidizing agent is extremely expensive and industrially disadvantageous. This agent produced by Kanto Kagaku Co., Ltd. costs ¥15,000 per 25 g (¥ means japanese Yen), or ¥81,096 per mol, and on the other hand, 34.5% aqueous hydrogen peroxide solution produced by Kanto Kagaku Co., Ltd. costs only ¥540 per 500 ml, or ¥106 per mol.

There is neither disclosure nor suggestion in the specification of the above patent that DMF, and hydrogen peroxide or a hypohalogenite are used in combination. The hypohalogenite includes a hypochlorite, a hypobromite, and hypoiodite.

There is disclosure in the specification of the above patent that in the manufacturing method of disulfides, hydrochloric acid treatment is carried out from completion of the chemical reaction to recrystallization, which is therefore widely known. Since in the method of the present invention a synthetic reaction of sulfides is carried out in the presence of a base, a stainless steel vessel, which is excellent in base resistance and relatively low cost, is advantageously used as a reaction vessel in the industry. However, hydrochloric acid eats the stainless steel and it is necessary that the reaction solution be transferred to an acid resistant glass-lined vessel before acid treatment. This method adds another reaction step of the reaction solution transfer, and requires an expensive glass-lined vessel. This is industrially disadvantageous. In view of the above, a simple and inexpensive acid treatment of a reaction solution has been strongly demanded.

It is difficult to simply manufacture sulfides at low cost and with high stability.

SUMMARY OF THE INVENTION

An object of the invention is to provide a method of simply manufacturing sulfides at low cost, with high stability and with high yield.

The sulfides manufactured according to the invention are useful as an additive for a silver halide photographic light sensitive material, medicines, agricultural pesticides, dyes and intermediates thereof.

When sulfides, manufactured according to the invention, are used as an image forming coupler for a silver halide color photographic light sensitive material, the coupler works as two equivalency coupler, resulting in silver saving, reduced affects due to formalin and high sensitivity.

The sulfides manufactured according to the invention are used in a silver halide photographic light sensitive material as a functional coupler, such as a development inhibitor releasing coupler or a bleach promoting agent releasing coupler.

DETAILED DESCRIPTION OF THE INVENTION

The above object of the invention has been attained by the following constitution:

1. A manufacturing method of sulfides (COUP-SR') wherein, after thiol (RSH) is oxidized to disulfide (RSSR), the disulfide (RSSR) is chemically modified without isolation of said disulfide to R'SSR', and the R'SSR' is reacted with COUP-H without isolation of said R'SSR' in the presence of a base and an oxidizing agent, wherein R and R' independently represent a substituent; COUP-H is a compound containing a carbon atom capable of being dissociated to be a nucleophilic species; and H is linked with a carbon atom capable of being said nucleophilic species.

2. The manufacturing method of sulfides described in 1 above, wherein COUP-H reacts with an oxidation product of a photographic developing agent to give a compound whose λmax is 400 to 750 nm in ethyl acetate.

3. The manufacturing method of sulfides described in 1 above, wherein COUP-H represents pyrazolones, dicyclic azoles, diketomethylenes, phenols, naphtols or enamines.

4. The manufacturing method of sulfides described in 1 above, wherein COUP-H represents 5-pyrazolones.

5. The manufacturing method of sulfides described in 1 above, wherein COUP-H represents dicyclic azoles.

6. The manufacturing method of sulfides described in 1 above, wherein COUP-H represents diketomethylenes.

7. The manufacturing method of sulfides described in 1 above, wherein COUP-H represents phenols.

8. The manufacturing method of sulfides described in 1 above, wherein COUP-H represents naphtols.

9. The manufacturing method of sulfides described in 1 above, wherein COUP-H represents enamines.

10. The manufacturing method of sulfides described in 1 above, wherein COUP-H represents 3-anilino-5-pyrazolones.

11. The manufacturing method of sulfides described in 1 above, wherein COUP-H represents 1-pentachlorophenyl-3-anilino-5-pyrazolones.

12. The manufacturing method of sulfides described in 1 above, wherein COUP-H contains 16 or more carbon atoms.

13. The manufacturing method of sulfides described in 1 above, wherein COUP-H is a compound represented by the following Formula (1):

Formula (1)

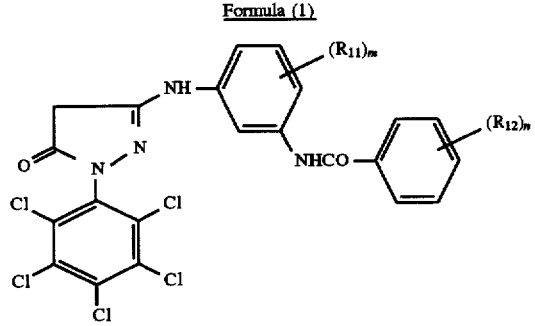

wherein $R_{11}$ and $R_{12}$ independently represent a substituent; m represents an integer of 0 to 4; and n represents an integer of 1 to 5.

14. The manufacturing method of sulfides described in 1 above, wherein said disulfide (R'SSR') is a symmetric diaryldisulfide.

15. The manufacturing method of sulfides described in 1 above, wherein R' in said disulfide (R'SSR') is a phenyl group having a substituent at an ortho-position regarding S.

16. The manufacturing method of sulfides described in 1 above, wherein at least one of R's in said disulfide (R'SSR') contains 12 or more carbon atoms.

17. The manufacturing method of sulfides described in 1 above, wherein said disulfide (R'SSR')is a compound represented by the following Formula (2'):

Formula (2')

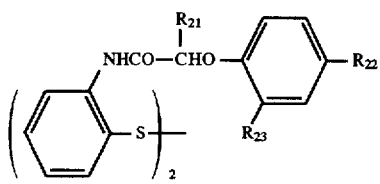

wherein $R_{21}$, $R_{22}$ and $R_{23}$ independently represent an alkyl group.

18. The manufacturing method of sulfides described in 1 above, wherein pKa of the base used in the reaction of R'SSR' and COUP-H is 4 to 20.

19. The manufacturing method of sulfides described in 1 above, wherein said thiol (RSH) is 2-aminothiophenol.

20. The manufacturing method of sulfides described in 1 above, wherein said oxidizing agent, which oxidizes said thiol (RSH) to said disulfide (RSSR), is hydrogen peroxide.

21. The manufacturing method of sulfides described in 1 above, wherein at least one of organic solvents, which are used in said reaction in which thiol (RSH) is oxidized to disulfide (RSSR), said reaction in which disulfide (RSSR) is chemically modified to disulfide (R'SSR')and said reaction in which R'SSR' is reacted with COUP-H, is used in common in said reactions.

22. The manufacturing method of sulfides described in 1 above, wherein a solvent used in reaction of R'SSR' with COUP-H is non-protonic polar solvents, esters, nitrites, water or a mixture thereof.

23. The manufacturing method of sulfides described in 1 above, wherein a reaction solvent used in reaction of R'SSR' with COUP-H is dimethylformamide, dimethylacetoamide, ethyl acetate, propyl acetate, acetonitrile, water or a mixture thereof.

24. The manufacturing method of sulfides described in 1 above, wherein a reaction solvent used in reaction of R'SSR' with COUP-H is dimethylformamide, a mixture solvent of dimethylformamide or dimethylformamide, ethyl acetate and water or a mixture of dimethylformamide, propyl acetate and water.

25. The manufacturing method of sulfides described in 1 above, wherein the water content of a reaction solvent used in reaction of R'SSR' with COUP-H is 1 wt % or more.

26. The manufacturing method of sulfides described in 1 above, wherein at least one of a reaction solvent used in reaction of R'SSR' with COUP-H is amides and the oxidizing agent used in reaction of R'SSR' with COUP-H is hydrogen peroxide.

27. The manufacturing method of sulfides described in 1 above, wherein the oxidizing agent used in reaction of R'SSR' with COUP-H is an oxygen molecule (air and oxygen positively introduced during reaction), sulfoxides, amine-N-oxides, hydrogen peroxide, ozone or nitroso compounds.

28. The manufacturing method of sulfides described in 1 above, wherein the oxidizing agent used in reaction of R'SSR' with COUP-H is a compound that oxidizes thiol to disulfide but does not further oxidize said disulfide.

29. The manufacturing method of sulfides described in 1 above, wherein the oxidizing agent used in reaction of R'SSR' with COUP-H is hydrogen peroxide.

30. The manufacturing method of sulfides described in 1 above, wherein the base used in reaction of R'SSR' with COUP-H is carbonates, caustic alkalis, organic bases, alkoxides, amines, aniline, guanidine or amidine.

31. The manufacturing method of sulfides described in 1 above, wherein the base used in reaction of R'SSR' with COUP-H is carbonates or caustic alkalis.

32. The manufacturing method of sulfides described in 1 above, wherein reaction temperature in reaction of R'SSR' with COUP-H is 0° C. to 40° C.

33. The manufacturing method of sulfides described in 1 above, wherein there is no halogenating agent present which halogenates R'SSR' or COUP-H during reaction.

34. A manufacturing method of sulfides comprising a reaction for synthesizing the sulfides (COUP-SR') on reaction of disulfide (R'SSR') with COUP-H in the presence of a base and an oxidizing agent in which the definition of R' and COUP-H is the same as those described in 1 above, wherein, until at least ⅔ of the COUP-H is consumed, the added amount of the oxidizing agent is controlled not to exceed an amount necessary to oxidize R'S⁻, produced in the reaction, to disulfide.

35. A manufacturing method of sulfides comprising a method for synthesizing the sulfides (COUP-SR') by reacting disulfide (R'SSR') with COUP-H in the presence of a base and an oxidizing agent in which the definition of R' and COUP-H is the same as those described in 1 above 1, wherein carboxylic acid or sulfonic acid treatment is carried out in a period between the end of reaction and recrystallization.

36. A manufacturing method of sulfides, wherein carbanion is reacted with disulfide in the presence of a hypohalogenite.

37. The manufacturing method of sulfides described in 36 above, wherein the carbanion is derived from pyrazolones, dicyclic azoles, diketomethylenes, phenols, naphtols or enamines.

38. The manufacturing method of sulfides described in 36 above, wherein the carbanion is derived from 5-pyrazolones.

39. The manufacturing method of sulfides described in 36 above, wherein the carbanion is derived from dicyclic azoles.

40. The manufacturing method of sulfides described in 36 above, wherein the carbanion is derived from diketomethylenes.

41. The manufacturing method of sulfides described in 36 above, wherein the carbanion is derived from phenols.

42. The manufacturing method of sulfides described in 36 above, wherein the carbanion is derived from naphtols.

43. The manufacturing method of sulfides described in 36 above, wherein the carbanion is derived from enamines.

44. The manufacturing method of sulfides described in 36 above, wherein the carbanion is derived from 3-anilino-5-pyrazolones.
45. The manufacturing method of sulfides described in 36 above, wherein the carbanion is derived from 1-pentachlorophenyl-3-anilino-5-pyrazolones.
46. The manufacturing method of sulfides described in 36 above, wherein the carbanion contains 16 or more carbon atoms.
47. The manufacturing method of sulfides described in 36 above, wherein the carbanion is derived from a compound represented by the following Formula (1):

Formula (1)

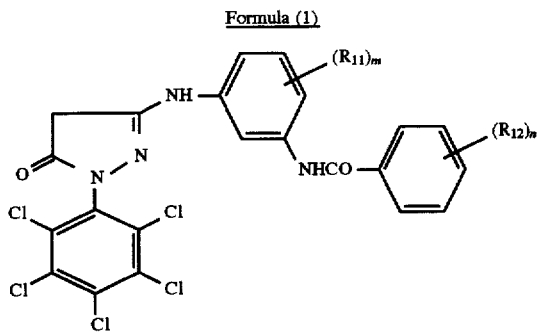

wherein $R_{11}$ and $R_{12}$ independently represent a substituent; m represents an integer of 0 to 4; and n represents an integer of 1 to 5.
48. The manufacturing method of sulfides described in 36 above, wherein the disulfide is a symmetric diaryldisulfide.
49. The manufacturing method of sulfides described in 36 or 48 above, wherein the disulfide has a substituent at an ortho-position regarding S.
50. The manufacturing method of sulfides described in 36 above, wherein the disulfide is a compound represented by the following Formula:

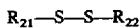

wherein at least one of $R_{21}$ and $R_{22}$ has 12 or more carbon atoms.
51. The manufacturing method of sulfides described in 36 above, wherein the disulfide is a compound represented by the following Formula (2):

Formula (2)

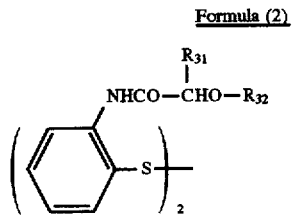

wherein $R_{31}$ represents an alkyl group; and $R_{32}$ represents an aryl group.
52. A manufacturing method of sulfides (COUP-SR') wherein, after thiol (RSH) is oxidized to disulfide (RSSR), the disulfide (RSSR) is chemically modified without isolation of said disulfide to disulfide (R'SSR'), and the R'SSR' is reacted with COUP-H without isolation of this disulfide in the presence of hypohalogenite, wherein R and R' independently represent a substituent different from each other; COUP-H is a compound containing a carbon atom capable of being dissociated to be a nucleophilic species; and H is linked with the carbon atom.
53. The manufacturing method of sulfides described in 52 above, wherein said thiol (RSH) is 2-aminothiophenol.
54. The manufacturing method of sulfides described in 52 above, wherein at least one of organic solvents, which are used in said reaction in which thiol (RSH) is oxidized to disulfide (RSSR), said reaction in which disulfide (RSSR) is chemically modified to disulfide (R'SSR') and said reaction in which said disulfide (R'SSR')is reacted with COUP-H, is used in common in said reactions. (R, R', COUP-H and H is the same as denoted in 52 above.)
55. The manufacturing method of sulfides described in 36 above, wherein a solvent used in reaction of the disulfide with the carbanion is non-protonic polar solvents, esters, nitrites, water or a mixture thereof.
56. The manufacturing method of sulfides described in 36 above, wherein a reaction solvent used in reaction of the disulfide with the carbanion is dimethylformamide, dimethylacetoamide, ethyl acetate, propyl acetate, acetonitrile, water or a mixture thereof.
57. The manufacturing method of sulfides described in 36 above, wherein a reaction solvent used in reaction of the disulfide with the carbanion is a mixture solvent of amides esters and water.
58. The manufacturing method of sulfides described in 36 above, wherein the water content of a reaction solvent used in reaction of the disulfide with the carbanion is 1 wt % or more.
59. The manufacturing method of sulfides described in 36 above, wherein reaction temperature in reaction of the disulfide with the carbanion is 0° C. to 40° C.
60. A manufacturing method of sulfides comprising a reaction for synthesizing the sulfides by reacting the disulfide with the carbanion in the presence of a hypohalogenite, wherein, until at least ⅔ of the carbanion is consumed, the added amount of said hypohalogenite is controlled not to exceed an amount necessary to oxidize mercaptan, produced during the reaction, to disulfide.
61. A manufacturing method of sulfides comprising a reaction for synthesizing the sulfides by reacting the disulfide with the carbanion in the presence of a hypohalogenite, wherein carboxylic acid or sulfonic acid treatment is carried out in a period between the end of reaction and recrystallization.
62. The manufacturing method of sulfides described in 36, 52, 60 or 61 above, wherein the hypohalogenite is hypochlorite.
63. A method of synthesizing 4-arylthio-5-pyrazolones, wherein 5-pyrazolones are reacted with disulfides in the presence of an alkali.
64. The method of synthesizing 4-arylthio-5-pyrazolones described in 63 above, wherein the alkali is carbonates or caustic alkalis.
65. The method of synthesizing 4-arylthio-5-pyrazolones described in 63 or 64 above, wherein the reaction is carried out further in the presence of an oxidizing agent.
66. The method of synthesizing 4-arylthio-5-pyrazolones described in 63, 64 or 65 above, wherein the reaction is carried out further in the presence of water.

67. The method of synthesizing 4-arylthio-5-pyrazolones described in 63, 64, 65 or 66 above, wherein the reaction is carried out further in the presence of a non-protonic polar solvent.

68. The method of synthesizing 4-arylthio-5-pyrazolones described in 63, 64, 65, 66 or 67 above, wherein the 5-pyrazolones is 3-anilino-5-pyrazolones.

69. The method of synthesizing 4-arylthio-5-pyrazolones described in 63 through 68 above, wherein the 5-pyrazolones is 1-pentachlorophenyl-3-anilino-5-pyrazolones.

70. The method of synthesizing 4-arylthio-5-pyrazolones described in 63 through 69 above, wherein the disulfides are symmetric diaryldisulfides having a substituent at an ortho-position.

71. The method of synthesizing 4-arylthio-5-pyrazolones described in 63 through 70 above, wherein acid treatment is carried out in a period between the end of reaction and recrystallization.

The invention will be detailed below.

The sulfides manufactured according to the invention are important compounds used for a magenta coupler in the photographic field, and also compounds useful as intermediates for many medicines, agricultural pesticides and dyes. When the silver halide photographic light sensitive material containing 5-pyrazolones is exposed and color developed, 5-pyrazolones react with the oxidation product of the color developing agent to produce corresponding azomethines and to form a magenta image.

When 4-arylthio-5-pyrazolones are used as a magenta coupler, there are many advantages that its coupling speed with the oxidation product is high, resulting in high sensitivity, density fluctuation due to pH fluctuation of developer rarely occurs, storage stability of developed images is improved, and yellow density increment (at unexposed portions) during storage is minimized.

Besides 4-arylthio-5-pyrazolones, the sulfides synthesized according to the invention are extremely important for photographic use.

This invention is a manufacturing method of sulfides (COUP-SR') in which, after thiol (RSH) is oxidized to disulfide (RSSR), the disulfide (RSSR) is chemically modified to R'SSR', without isolation of said disulfide and the R'SSR' is reacted with COUP-H in the presence of a base and an oxidizing agent without isolation of said R'SSR'. U.S. Pat. No. 5,405,969, cited above, employs isolated R'SSR'. On the other hand, the present invention provides a method of easily obtaining, without isolation of RSSR as well as R'SSR, the objective compound sulfides with high yield and with certainty. This is a first advantage of the invention. The second advantage of the invention is to minimize undesirable side reactions due to an oxidizing agent by controlling an addition speed of the oxidizing agent.

R and R' in the invention independently represent a substituent, and the example thereof includes the same as the substituent represented by $R^1$, $R^2$ and $R^3$ in formula (3) described later, and is preferably an aryl group. The term "chemically modified" referred to in the invention means to convert at least one substituent to another substituent, and does not mean a change in equilibrium condition such as tautomerism or dissociation.

COUP-H (also called a coupling compound used) in the invention is a coupling compound containing a carbon atom capable of a nucleophilic species by dissociation. The pKa of the coupling compound is preferably 3–14.

It is preferable that the carbanion is an anion derived from a compound represented by Formula (1), or the COUP-H or the coupling compound is a compound represented by Formula (1), since the invention is markedly effected. The term "derived from a compound" above referred to means "produced by dissociation of proton from the compound".

In formula (1), $R_{11}$ and $R_{12}$ independently represent a substituent, and concretely the substituent includes the same as the substituent represented by $R^1$ and $R^2$ in formula (3) described later. $R_{11}$ and $R_{12}$ are preferably a halogen atom or an alkoxy group, and more preferably a halogen atom.

m represents an integer of 0 through 4, and preferably 1.

n represents an integer of 1 through 5, and preferably 2.

More concretely, COUP-H represents pyrazolones, dicyclic azoles, diketomethylenes, phenols, naphtols or enamines.

In the invention, pyrazolones are used as raw material. The pyrazolones are preferably 3-anilino-5-pyrazolones, and more preferably 1-pentachlorophenyl-3-anilino-5-pyrazolones, since the invention is markedly effected.

The present invention is advantageous, since, when employing COUP-H containing 16 or more carbon atoms, sulfides (COUP-SR') is lowered in its crystallinity, cause side reactions, and are difficult to obtain with high yield.

When the carbanion is derived from a compound represented by formula (1), or compound COUP-H is represented by formula (1), the method of the invention is advantageously applied, since the COUP-H has low solubility. The method of the invention is especially advantageous when DMF is used as a solvent.

The disulfides (R'SSR'), used as raw material in the method of the invention, are preferably symmetric diaryldisulfides (two R's are the same group), since they give high a reaction rate and produce single sulfides. The disulfides (R'SSR')as raw material in the method of the invention, when R' is a phenyl group having a substituent at an ortho-position regarding S, the R's contain 12 or more carbon atoms or said disulfide (R'SSR')is a compound represented by formula (2) or (2'), are markedly effected and preferable in the method of the invention, since the disulfides (R'SSR')have low crystallinity and are difficult to isolate.

In Formula (2) above, $R_{31}$ represents an alkyl group, and $R_{32}$ represents an aryl group. Specifically, the alkyl group of $R_{31}$ includes the same as the alkyl group represented by $R^1$ or $R^2$ of Formula (3) described later, and the aryl group of $R_{32}$ includes the same as the aryl group represented by $R^3$ of Formula (3) described later.

$R_{21}$, $R_{22}$ and $R_{23}$ in formula (2') independently represent an alkyl group, and concretely represent the alkyl group represented by R' and $R^2$ in formula (3) described later.

The base employed in the invention is not limited, but is preferably carbonates or caustic alkalis in terms of yield, cost and workability, and is more preferably carbonates. Sodium carbonates or potassium carbonates are especially preferable. Organic bases such as triethylamine, dimethylaniline, pyridine and sodium methylate are applicable.

The addition amount of the base used is not specifically limited, but 0.1 to 10 is preferably 0.1 to 10 equivalent, and is more preferably 1 to 6 equivalent based on one equivalent COUP-H used.

The solvent used in the invention includes esters (for example, ethylacetate or isopropylacetate), aromatic hydrocarbons (for example, benzene and toluene), halogenated hydrocarbons (for example, chloroform and dichloromethane), non-protonic polar solvents (for example, dimethylformamide, dimethylacetoamide, dimethylsulfoxide and N-methylpyrrolidinone), alcohols (for example, methanol, ethanol and isopropanol), ethers (for example, tetrahydrofurane and dioxane), nitrites (for example, acetonitrile) and water. The solvent is not specifically limited, but is preferably a solvent having a boiling point of 50° to 140° C. The solvent is preferably non-protonic polar solvents, esters or a mixture thereof in that the effect of the invention is easily attained. The solvent is more preferably dimethylformamide, dimethylacetoamide, ethyl acetate, propyl acetate, acetonitrile, water or a mixture.

When a mixture solvent is used, the mixture solvent preferably contains water. Two phase reaction can be carried out using a mixture solvent containing two immiscible solvents.

The first and second oxidizing agents may be any agent capable of oxidizing thiols to disulfides, and are not specifically limited, but are preferably an oxygen molecule (air and oxygen positively introduced during reaction), sulfoxides, amine-N-oxides, hydrogen peroxide, ozone, hypohalogenite or nitroso compounds, in view of cost and reactivity, and more preferably hydrogen peroxide or hypohalogenite.

The hypohalogenite used in the invention is not limited, but hypochlorite or hypobromite is preferable in view of high reaction efficiency and availability, and hypochlorite is more preferable.

The cation constituting the hypohalogenite is not limited, but a sodium, potassium, magnesium or calcium ion is preferable in view of high reaction efficiency, and a sodium or magnesium ion is preferable in view of solubility.

In view of the above, an aqueous sodium hypochlorite solution is most preferably used.

The oxidizing agent used in oxidizing thiol (RSH) to synthesize disulfide (RSSR) may be hypohalogenite or other oxidizing agents such as an aqueous hydrogen peroxide solution.

The addition method of the oxidizing agent is not specifically limited, but when the addition speed of the oxidizing agent is controlled to be an amount not more than the amount necessary to oxidize R'S- produced during reaction to R'SS R', side reaction due to the oxidizing agent is minimized, which is advantageous. It is specifically advantageous when dimethylformamide is used as a reaction solvent.

The reaction temperature is not specifically limited, but it is preferably 0° to 40° C. in view of reactivity, yield, cost and workability.

The term "without isolation of said disulfide from the solution" referred to in the invention means that said disulfide is not isolated from the solution as a solid disulfide.

The carboxylic acids or sulfonic acids used in acid treatment in the invention are not specifically limited. The example of carboxylic acids includes acetic acid, propionic acid and benzoic acid, and acetic acid is preferable. The sulfonic acids include alkyl sulfonic acids and arylsulfonic acids, and the example thereof includes methane sulfonic acid and p-toluene sulfonic acid.

The carboxylic acids or sulfonic acids used in acid treatment in the invention are preferably water soluble. Carboxylic acids are more preferable, and acetic acid is most preferable.

The synthesizing method of the invention is applied to various sulfides. The sulfides, 4-arylthio-5-pyrazolones, which are preferably used in the synthesizing method of the invention, include a compound represented by the following formula (3):

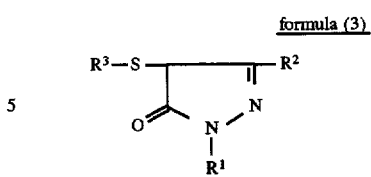

formula (3)

wherein $R^1$ and $R^2$ independently represent a hydrogen atom or a substituent; and $R^3$ represents an aryl group.

In formula (3), the substituent represented by $R^1$ and $R^2$ includes preferably an alkyl, cycloalkyl, aryl, heterocyclic, alkylcarbonyl, alkylsulfonyl, arylcarbonyl, alkoxycarbonyl, aryloxycarbonyl, arylsulfonyl, alkylsulfinyl, arylsulfinyl, carbamoyl, sulfamoyl, cyano, amino, alkylamino, arylamino, arylcarbonylamino, arylaminocarbonyl, sulfonamido, amido, ureido, thioureido, alkoxy, aryloxy, alkylthio, arylthio, carboxy, sulfo, and hydroxy group and a halogen atom.

The alkyl group represented by $R^1$ and $R^2$ includes a methyl, ethyl, propyl, i-propyl, t-butyl, pentyl, hexyl, octyl, 2-ethylhexyl, dodecyl, pentadecyl and eicosyl group. The alkyl group includes an alkyl group having a substituent, and the substituent includes a halogen atom (for example, a fluorine, chlorine, bromine and iodine atom), aryl (for example, phenyl or naphtyl), cycloalkyl (for example, cyclopentyl or cyclohexyl), heterocyclic (for example, pyrrolidyl or pyridyl), a sulfinic acid group, carboxy, sulfo, nitro, cyano, hydroxy, mercapto, amino (for example, amino or diethylamino), alkyloxy (for example, methyloxy, ethyloxy, butyloxy, octyloxy, or iso-propyloxy), aryloxy (for example, phenyloxy or naphtyloxy), carbamoyl (for example, aminocarbonyl, methylcarbamoyl, pentylcarbamoyl or phenylcarbamoyl), amido (for example, methylamido, benzamido, or octylamido), aminosulfonylamino (for example, aminosulfonylamino, methylaminosulfonylamino, or anilinosulfonylamino group), sulfamoyl (for example, sulfamoyl, methylsulfamoyl, phenylsulfamoyl or butylsulfamoyl), sulfonamido (for example, methanesulfonamido, heptanesulfonamido or benzenesulfonamido), sulfinyl (for example, alkylsulfinyl such as methylsulfinyl, ethylsulfinyl or octylsulfonyl or arylsulfinyl such as phenylsulfinyl), alkyloxycarbonyl (for example, methyloxycarbonyl, ethyloxycarbonyl, 2-hydroxyethyloxycarbonyl group or octyloxycarbonyl), aryloxycarbonyl (for example, phenyloxycarbonyl or naphtyloxycarbonyl), alkylthio (for example, methylthio, ethylthio or hexylthio), arylthio (for example, phenylthio or naphtylthio), alkylcarbonyl (for example, acetyl, ethylcarbonyl, butylcarbonyl or octylcarbonyl), arylcarbonyl (for example, benzoyl, methanesulfonamidobenzoyl, p-carboxybenzoyl or naphtoyl), cyano, ureido (for example, methylureido or phenylureido) and thioureido (for example, methylthioureido or phenylthioureido).

The aryl group represented by $R^1$ and $R^2$ includes phenyl, 2,3,4,5,6-petachlorophenyl and nathtyl. The aryl group includes an aryl group having a substituent, and the substituent includes the alkyl group represented by $R^1$ and $R^2$ and the same as those denoted above as the substituent of the alkyl group represented by $R^1$ and $R^2$.

The heterocyclic group represented by $R^1$ and $R^2$ includes pyridyl (2-pyridyl, 3-pyridyl, 4-pyridyl, 5-carboxy-2-pyridyl, 3,5-dichloro-2-pyridyl, 4,6-dimethyl-2-pyridyl, 6-hydroxy-2-pyridyl, 2,3,5,6-tetrafluoro-4-pyridyl, 3-nitro-2-pyridyl etc.), oxazolyl (5-carboxy-2-benzoxazolyl, 2-benzoxazolyl, 2-oxazolyl etc.), thiazolyl (5-sulfamoyl-2-benzothiazoyl, 2-benzothiazoyl, 2-thiazoyl etc.), imidazolyl (1-methyl-2-imidazolyl, 1-methyl-5-carboxy-2-imidazolyl etc.), furyl (3-furyl etc.), pyrrolyl (3-pyrrolyl etc.), thienyl (2-thienyl etc.), pyrazinyl (2-pyrazinyl etc.), pyrimidinyl (2-pyrimidinyl, 4-chloro-pyrimidinyl etc.), pyridazinyl (2-pyridazinyl etc.), isooxazolyl (3-isooxazolyl etc.), selenazolyl (5-carboxy-2-selenazolyl etc.), sulfolanyl (3-sulfolanyl etc.), piperidinyl (1-methyl-3-pyperidinyl etc.), pyrazolyl (3-pyrazolyl etc.) and tetrazolyl (1-methyl-5-tetrazolyl etc.), and the heterocyclic group includes a heterocyclic group having a substituent, and the substituent includes the alkyl group represented by $R^1$ and $R^2$ and the same as those denoted above as the substituent of the alkyl group represented by $R^1$ and $R^2$.

The cycloalkyl group represented by $R^1$ and $R^2$ includes cyclopropyl, cyclobutyl, cyclopentyl and cyclohexyl.

The alkylcarbonyl group represented by $R^1$ and $R^2$ includes methylcarbonyl, ethylcarbonyl, isopropylcarbonyl, t-butylcarbonyl, octylcarbonyl, and dodecylcarbonyl.

The arylcarbonyl group represented by $R^1$ and $R^2$ includes phenylcarbonyl and naphtylcarbonyl.

The alkoxycarbonyl group represented by $R^1$ and $R^2$ includes ethoxycarbonyl, i-propoxycarbonyl, t-butoxycarbonyl, pentyloxycarbonyl and dodecyloxycarbonyl.

The aryloxycarbonyl group represented by $R^1$ and $R^2$ includes phenyloxycarbonyl and naphtyloxycarbonyl.

The alkylsulfonyl group represented by $R^1$ and $R^2$ includes methylsulfonyl, ethylsulfonyl, isopropylsulfonyl, t-butylsulfonyl, octylsulfonyl, and octadecylsulfonyl.

The arylsulfonyl group represented by $R^1$ and $R^2$ includes phenylsulfonyl and naphtylsulfonyl.

The alkylsulfinyl group represented by $R^1$ and $R^2$ includes methylsulfinyl, ethylsulfinyl, isopropylsulfinyl, t-butylsulfinyl, octylsulfinyl, and dodecylsulfinyl.

The arylsulfinyl group represented by $R^1$ and $R^2$ includes phenylsulfinyl and naphtylsulfinyl.

The carbamoyl group represented by $R^1$ and $R^2$ includes aminocarbonyl, methylcarbamoyl, ethylcarbamoyl, isopropylcarbamoyl, t-butylcarbamoyl, dodedecylcarbamoyl, phenylcarbamoyl, 2-pyridylcarbamoyl, benzylcarbamoyl, morpholinocarbamoyl, and piperazinocarbamoyl.

The sulfamoyl group represented by $R^1$ and $R^2$ includes aminosulfonyl, methylsulfamoyl, ethylsulfamoyl, isopropylsulfamoyl, t-butylsulfamoyl, dodedecylsulfamoyl, phenylsulfamoyl, 2-pyridylsulfamoyl, 4-pyridylsulfamoyl, morpholinosulfamoyl and piperazinosulfamoyl.

The amino group represented by $R^1$ and $R^2$ includes amino, methylamino, ethylamino, isopropylamino, t-butylamino, octylamino, dodedecylamino, dimethylamino, anilino, naphtylamino, morpholino and piperazino, and anilino is preferable in the invention.

The sulfonamide group represented by $R^1$ and $R^2$ includes methylsulfonamide, ethylsulfonamide, isopropylsulfonamide, t-butylsulfonamide, dodecylsulfonamide, phenylsulfonamide, and naphtylsulfonamide.

The amide group represented by $R^1$ and $R^2$ includes methylcarbonylamide, ethylcarbonylamide, isopropylcarbonylamide, t-butylcarbonylamide, dodecylcarbonylamide, phenylcarbonylamide, and naphtylcarbonylamide.

The alkylamino group represented by $R^1$ and $R^2$ includes methylamino, dimethylamino, ethylamino, diethylamino, isopropylamino, t-butylamino and octylamino.

The arylamino group represented by $R^1$ and $R^2$ includes anilino and naphtylamino.

Each group represented by $R^1$ and $R^2$ includes those having a substituent, and the substituent includes the alkyl group represented by $R^1$ and $R^2$ and the same as those denoted above as the substituent of the alkyl group represented by $R^1$ and $R^2$.

The aryl group represented by $R^3$ includes phenyl and naphtyl. The aryl group represented by $R^1$ and $R^2$ includes a group having a substituent, and the substituent includes the alkyl group represented by $R^1$ and the same as those denoted above as the substituent of the alkyl group represented by $R^1$.

In the manufacturing method of the invention, 4-arylthio-5-pyrazolones are preferably used. The preferable example of 4-arylthio-5-pyrazolones will be shown below. In 4-arylthio-5-pyrazolones represented by formula (3), $R^2$ preferably represents the following group:

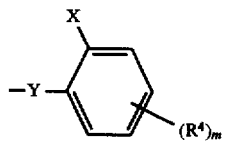

wherein Y represents a divalent group, for example, —O—, —$NR^5$, alkylene, —$NR^6CO$—, —$CONR^7$— or —$NR^5CONR^9$, in which $R^4$ through $R^9$ represent the same as $R^1$, preferably —NH— or —NHCO—, more preferably —NH—; X represents a methoxy group or a chlorine atom; and m is an integer of 1 to 4.

The more preferable example of 4-arylthio-5-pyrazolones applicable to the manufacturing method of the invention is a compound (also called a magenta coupler) represented by the following Formula (4):

Formula (4)

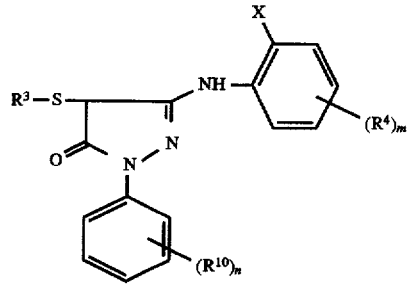

wherein $R^3$, $R^4$, X and m independently represent the same as those denoted in $R^3$, $R^4$, X and m of formula (3), respectively; $R^{10}$ represents the same as those denoted in the substituent of the aryl group of $R^1$; and n is an integer of 0 to 5.

It is most preferable that $R^{10}$ represents a chlorine atom, and n is 5.

The exemplified compounds preferably prepared according to the manufacturing method of the invention will be shown below, but the invention is not limited thereto.

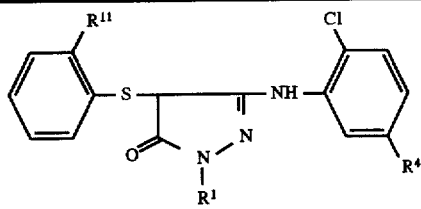
| No. | R¹¹ | R¹ | R⁴ |
|---|---|---|---|
| 1 | —NHCOCH(C₂H₅)O-[2,4-di-t-C₅H₁₁-phenyl] | 2,3,4,5,6-pentachlorophenyl | —NHCO-[2,6-di-Cl-phenyl] |
| 2 | " | " | —NHCO-[2,6-di-OCH₃-phenyl] |
| 3 | —NHCOC₁₃H₂₇ | " | —NHCO-[2,6-di-Cl-phenyl] |
| 4 | —NHCOCH(C₂H₅)O-[2,4-di-t-C₅H₁₁-phenyl] | " | —SO₂C₁₂H₂₅ |
| 5 | " | 2,4,6-trichlorophenyl | —NHCOC₁₃H₂₇ |
| 6 | " | " | —NHCO-[2,6-di-Cl-phenyl] |
| 7 | " | " | —NHCO-[2,6-di-OCH₃-phenyl] |
| 8 | —NHCOC₁₃H₂₇ | " | —NHCO-[2,6-di-Cl-phenyl] |

-continued

| No. | R¹² structure | middle structure | right group |
|---|---|---|---|
| 9 | —NHCOCH(C₂H₅)—[2,4-di-C₅H₁₁(t)-phenyl] | 3,5-dichloro-4-methylphenyl with SO₂N-morpholine | —NHCOC₁₃H₂₇ |
| 10 | " | 3,5-dichloro-4-methylphenyl with CN | " |
| 11 | —NHCOCH(C₂H₅)—[2,4-di-C₅H₁₁(t)-phenyl] | 2,5-dichloro-3-methyl-6-methoxyphenyl (OCH₃) | —CO₂C₁₆H₃₃ |

Structure:

R¹²—CH(C(=O))—N(R¹)—N=C—NH—(2-Cl, 5-R⁴-phenyl)

| No. | R¹² | R¹ | R⁴ |
|---|---|---|---|
| 12 | 2-OC₄H₉-4-C(CH₃)₂CH₂C(CH₃)₃-phenyl-S— | 3,5-dichloro-4-methylphenyl with CN | —NHCOCH₂CH(C₂H₅)C₄H₉ |
| 13 | " | 3,5-dichloro-4-methylphenyl with SO₂N-morpholine | —SO₂C₁₂H₂₅ |
| 14 | " | 2,4,6-trichlorophenyl (methyl) | —NHCOC₁₃H₂₇ |
| 15 | (t)C₅H₁₁-, C₅H₁₁(t)- phenyl-OCH(C₂H₅)-C(=O)NH-(4-phenyl-S—) | 2,3,4,5,6-pentachlorophenyl | —NHCOCH(C₂H₅)—[2,4-di-C₅H₁₁(t)-phenyl] |

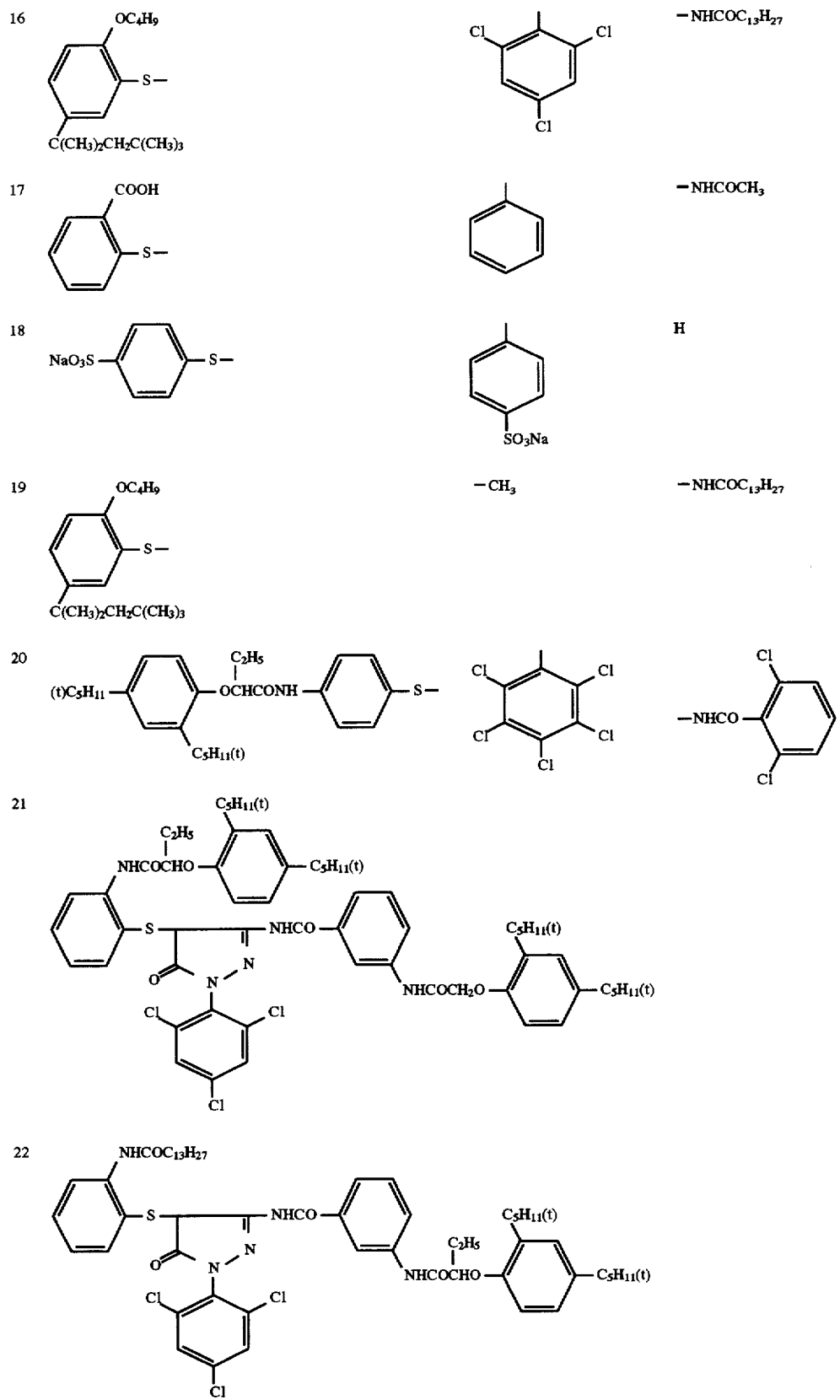

-continued
23
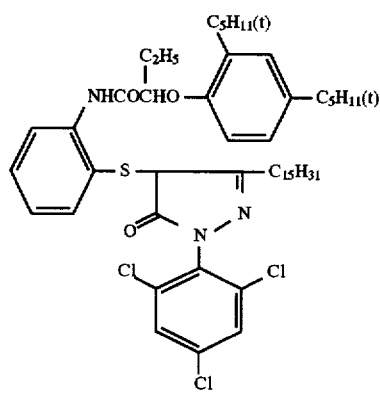
24
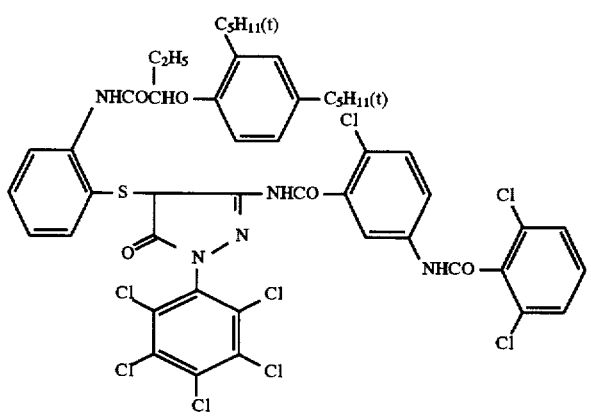
25
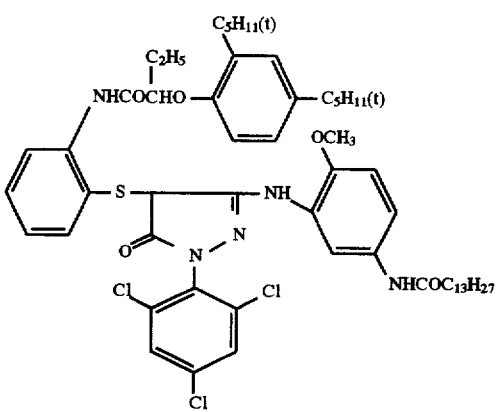

-continued

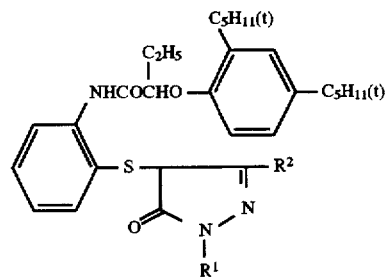

| No. | R² | R¹ |
|---|---|---|
| 26 | —⌬—Cl | 2,4,6-trichlorophenyl |
| 27 | —COC₁₃H₂₇ | " |
| 28 | —CO—⌬ | " |
| 29 | —CO₂C₁₂H₂₅ | " |
| 30 | —CONHCH₂CH(C₈H₁₇)(C₈H₁₇) | phenyl |
| 31 | —CN | 2,4,6-trichlorophenyl |
| 32 | —N(CH₃)₂ | " |
| 33 | —NHCONHC₁₃H₂₇ | " |
| 34 | —OC₁₂H₂₅ | " |
| 35 | —COOH | 4-SO₃Na-phenyl |
| 36 | —C₈H₁₇ | —CH₃ |

| No. | $R^2$ | $R^1$ |
|---|---|---|
| 26 | 4-chlorophenyl | 2,4,6-trichlorophenyl |
| 27 | $-COC_{13}H_{27}$ | " |
| 28 | $-CO-C_6H_5$ | " |
| 29 | $-CO_2C_{12}H_{25}$ | " |
| 30 | $-CONHCH_2CH(C_8H_{17})_2$ | phenyl |
| 31 | $-CN$ | 2,4,6-trichlorophenyl |
| 32 | $-N(CH_3)_2$ | " |
| 33 | $-NHCONHC_{13}H_{27}$ | " |
| 34 | $-OC_{12}H_{25}$ | " |
| 35 | $-COOH$ | 4-$SO_3Na$-phenyl |
| 36 | $-C_8H_{17}$ | $-CH_3$ |

-continued
No 37
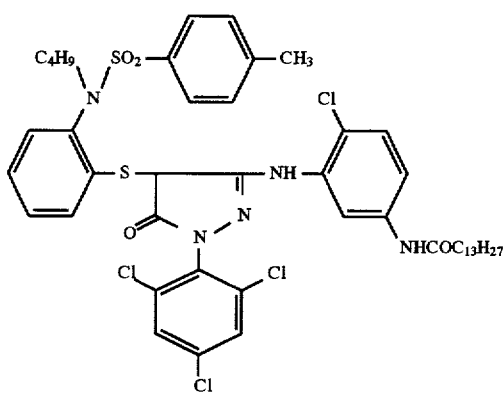
No 38
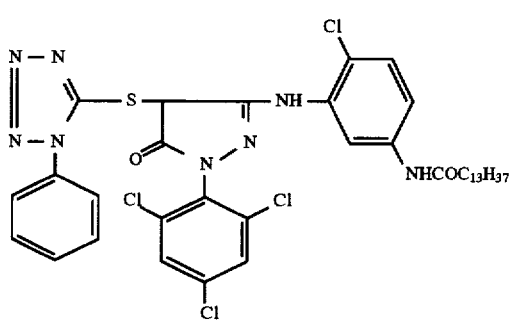
No 39
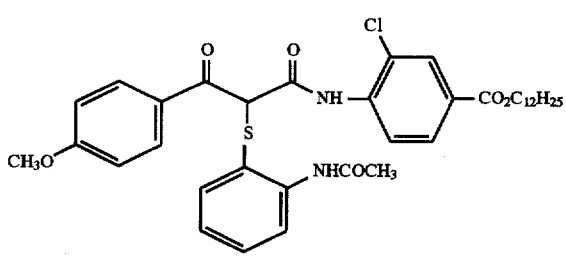
No 40
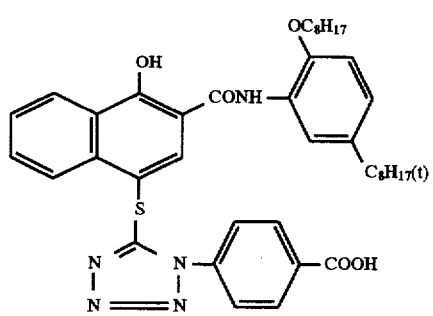
No 41
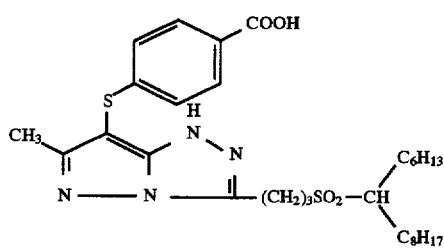

| | |
|---|---|
| No 42 | 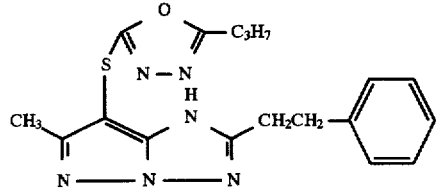 |
| No 43 | 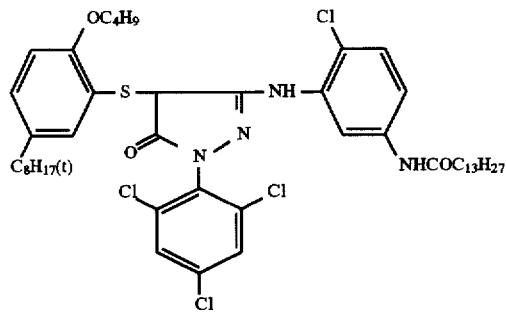 |
| No 44 | 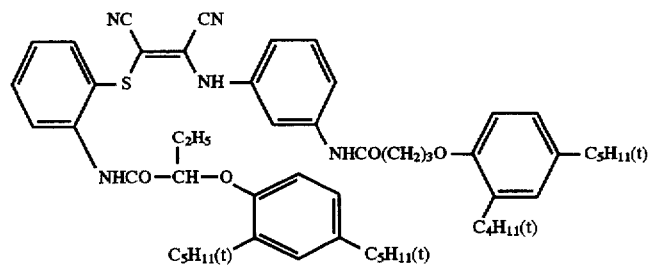 |
EXAMPLES
The invention will be explained in the following examples, but is not limited thereto.
Example 1 (Synthesis of exemplified compound 1)
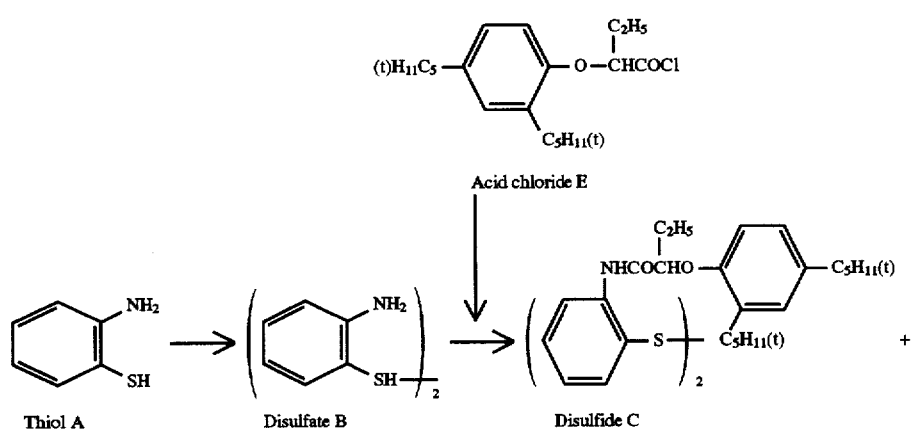

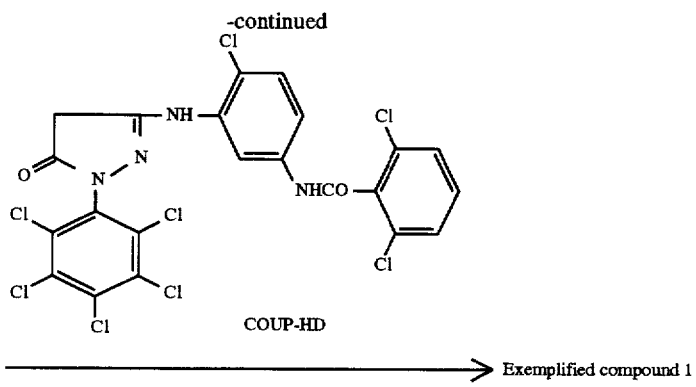

COUP-HD

→ Exemplified compound 1

Thiol A of 40.0 g were dissolved in 1300 ml of ethyl acetate, 17.0 g of a 35% hydrogen peroxide solution were dropwise added thereto, and then stirred at room temperature for 3 hours. A solution, in which 54 g of potassium carbonate are dissolved in 300 ml water, was added to the resulting solution and then 130.6 g of acid chloride E were dropwise added.

After the dropwise addition, the solution was heated to 50° to 60° C., and allowed to cool. To the cooled solution were added in this order 420 ml of dimethylformamide, 188 g of COUP-HD and a solution in which 60g of potassium carbonate was dissolved in 200 ml water. One part of five parts into which 8.6 g of a 35% hydrogen peroxide aqueous solution were divided was added thereto every hour at room temperature while stirring. Two hours after the addition of the hydrogen peroxide aqueous solution, 300 ml of water were added, and the organic phase solution was separated. The organic phase solution was added with 60 ml of acetic acid and a sodium chloride solution, and the organic phase solution was again separated. This process was repeated two more times, and the organic phase solution was washed three times with a sodium chloride solution. The solvents of the washed solution were removed by vacuum evaporation. The residue was recrystallized from 1.8 liter of ethanol to obtain faint pale pink crystals.

The crystals were further suspended in 1900 ml ethanol while heated and washed to obtain 265 g of faint pale pink crystals (yield: 85%).

The crystals were identified to be Exemplified Compound 1 according to NMR spectrum and mass spectrum analysis.

As is apparent from the above, an objective compound, such as Exemplified Compound 1 is synthesized with high yield according to the easy and simple procedures described above.

Example 2

Procedures were carried out in the same manner as in Example 1, except that raw materials (without change of their mole concentration) were varied to obtain exemplified compounds 2, 3, 4, 5, 9 through 13, 15, 16, 20 through 24, 37 and 43. The yield is shown in Table 1.

TABLE 1

| 4-Arylthio-5-pyrazolones | Yield (%) |
|---|---|
| Exemplified compound 2 | 80.9 |
| Exemplified compound 3 | 79.1 |
| Exemplified compound 4 | 75.0 |

TABLE 1-continued

| 4-Arylthio-5-pyrazolones | Yield (%) |
|---|---|
| Exemplified compound 5 | 72.3 |
| Exemplified compound 9 | 73.0 |
| Exemplified compound 10 | 71.8 |
| Exemplified compound 11 | 74.0 |
| Exemplified compound 12 | 72.0 |
| Exemplified compound 13 | 73.5 |
| Exemplified compound 15 | 78.3 |
| Exemplified compound 16 | 73.9 |
| Exemplified compound 20 | 80.5 |
| Exemplified compound 21 | 63.0 |
| Exemplified compound 22 | 61.9 |
| Exemplified compound 23 | 60.1 |
| Exemplified compound 24 | 70.2 |
| Exemplified compound 37 | 74.0 |
| Exemplified compound 43 | 73.0 |

Comparative Example 1

(Synthesis of Disulfide C)

Thiol A of 40.0 g were dissolved in 1300 ml of ethyl acetate, 17.0 g of a 35% hydrogen peroxide aqueous solution were dropwise added thereto, and then was stirred at room temperature for 5 hours. The solution in which 54 g of potassium carbonate are dissolved in 200 ml water was added to the resulting solution and then 130.6 g of acid chloride E were dropwise added.

After the dropwise addition, the solution was heated and reacted at 50° to 60° C. for 2 hours. Thereafter, the organic phase solution was washed two times with a sodium chloride solution, and the solvents of the washed solution were removed by vacuum evaporation. The residue was recrystallized from an ethyl acetate-acetonitrile mixture solvent to obtain 106 g of yellow, needle crystals (yield 78%).

The crystals were identified to be Disulfide C according to NMR spectrum and mass spectrum analysis.

Synthesis of Exemplified Compound 1

To the above obtained disulfide C were added in this order 1014 ml of ethyl acetate, 328 ml of dimethylformamide, 146.6 g of COUP-HD and a solution in which 46.8 g of potassium carbonate was dissolved in 156 ml water. One part of five parts into which 6.7 g of a 35% hydrogen peroxide aqueous solution were divided was added every one hour at room temperature while stirring.

Two hours after the addition of the hydrogen peroxide aqueous solution, 234 ml of water were added, and divided into two phases. The organic phase solution was purified in the same manner as in Example 1 to obtain 206 g of faint pink white crystal (yield: 85%).

The crystal was identified to be Exemplified Compound 1 according to NMR spectrum and mass spectrum analysis. The total yield is 66.3%.

This method requires an extra one process and lowers the yield of Exemplified compound 1 as compared with the method of Example 1. As is apparent from the above, the Example 1 method is more advantageous.

Example 3

Example 1 was repeated, except that a part of water was not used as a reaction solvent, yield of an objective compound (Exemplified compound 1), which was measured according to HPLC, was 65%.

This method attains one object of the invention in that an objective compound is easily obtained, but yield is inferior to Example 1. This shows that the invention is markedly effected by employing water as a reaction solvent.

Example 4

Example 1 was repeated, except that DMF was not used, yield of an objective compound (Exemplified compound 1), which was measured according to HPLC, was 75%.

This method attains one object of the invention in that an objective compound is easily obtained, but yield is inferior to Example 1. This shows that the invention is markedly effected by employing DMF as a reaction solvent.

Example 5

Example 1 was repeated, except that acid treatment of the organic phase after the synthesis of sulfide was not carried out, and isolation yield was 35%.

This method attains one object of the invention in that an objective compound is easily obtained, but the isolation yield is inferior to Example 1. This shows that the acid treatment improves yield.

Example 6 (Synthesis of exemplified compound 1)

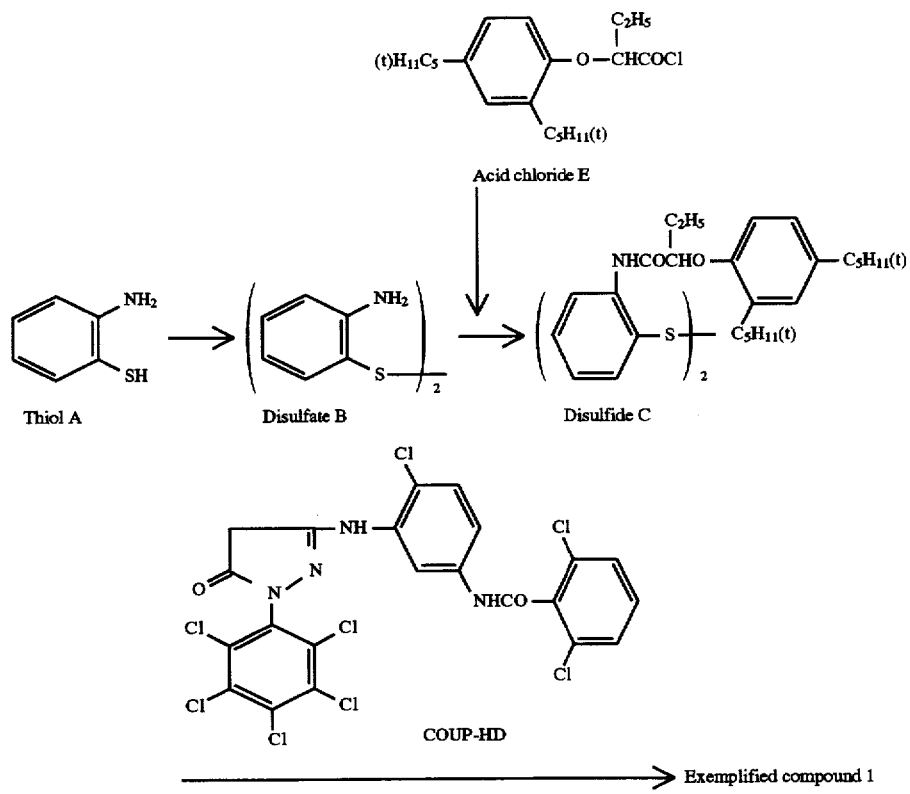

Thiol A of 6.9g were dissolved in 210 ml of ethyl acetate, 2.71 g of a 35% hydrogen peroxide solution were dropwise added thereto, and then was stirred at room temperature for 1.5 hours. A solution in which 8.15 g of potassium carbonate were dissolved in 37.5 ml water was added to the resulting solution and then 23.15 g of acid chloride E were dropwise added.

After the dropwise addition, the solution was heated to 25° to 40° C., and allowed to cool. After the solution was allowed to stand for 15 hours, the solution was added with in this order 32.3 g of COUP-HD, 150 ml of dimethylformamide, and a solution in which 10.35 g of potassium carbonate was dissolved in 25 ml water. After stirred for 2 hours at room temperature, each part of three parts into which 3.32 g of a sodium hypochlorite aqueous solution containing an effective chlorine amount of 12% were divided was added every 1.5 hours. After the resulting solution was stirred for 3 hours at room temperature, four 3.325 g of a sodium hypochlorite aqueous solution containing the same concentration as above were added in four hours. Two hours after the addition of the sodium hypochlorite aqueous solution, 100 ml of water were added, and an organic phase solution was separated. The resulting organic phase solution was added with 20 ml of acetic acid and a sodium chloride solution, and the organic phase solution was separated. This process was repeated two more times, and the organic phase solution was washed three times with a sodium chloride solution. The solvents of the washed solution were removed by vacuum evaporation. The residue was recrystallized from 310 ml of ethanol to obtain faint pale pink crystals.

The crystals were further suspended in 330 ml ethanol while heated and washed to obtain 45.8 g of faint pale pink crystals (yield: 85%).

The crystals were identified to be Exemplified Compound 1 according to NMR spectrum and mass spectrum analysis.

As is apparent from the above, an objective compound, such as Exemplified Compound 1 is synthesized with high yield according to the easy and simple procedures described above.

Example 7

Procedures were carried out in the same manner as in Example 6, except that used materials (without change of their mole concentration) were varied to obtain exemplified compounds 5, 9, 14, 16, 21, 24, and 37. The yield is shown in Table 2.

TABLE 2

| 4-Arylthio-5-pyrazolones | Yield (%) |
|---|---|
| Exemplified compound 5 | 81.0 |
| Exemplified compound 9 | 80.3 |
| Exemplified compound 14 | 79.5 |
| Exemplified compound 16 | 77.0 |
| Exemplified compound 21 | 69.9 |
| Exemplified compound 24 | 72.1 |
| Exemplified compound 37 | 75.6 |

Example 8

Example 6 was repeated, except that DMF was not used, yield of an objective compound (Exemplified Compound 1), which was measured according to HPLC, was 74%.

This method attains one object of the invention in that an objective compound is easily obtained, but yield is inferior to Example 6. This shows that the invention is markedly effected by employing DMF as a reaction solvent.

Example 9

Example 6 was repeated, except that the acid treatment of the organic phase solution after the synthesis of sulfide was not carried out, and isolation yield was 35%.

This method attains one object of the invention in that an objective compound is easily obtained, but the isolation yield is inferior to Example 6. This shows that the acid treatment improves yield.

As is apparent from the above, sulfides useful for industry are industrially synthesized with stability, safety, non-pollution, low cost and high yield according to the simple procedures of the invention.

What is claimed is:

1. A method of manufacturing a sulfide comprising the steps of:

dissolving a thiol in a solvent to form a solution;

oxidizing the thiol to a disulfide in the presence of a first oxidizing agent in the solution;

reacting the disulfide with a coupling compound in the presence of a base and a second oxidizing agent, without isolation of said disulfide from the solution, to form a reaction mixture in which the sulfide is produced; and obtaining said sulfide.

2. The method of claim 1, wherein said coupling compound is a compound which reacts with an oxidation product of a photographic developing agent to give a compound having a λmax of 400 to 750 nm in ethyl acetate.

3. The method of claim 1, wherein said coupling compound is pyrazolones, dicyclic azoles, diketomethylenes, phenols, naphtols or enamines.

4. The method of claim 1, wherein said coupling compound is 5-pyrazolones.

5. The method of claim 1, wherein said coupling compound is 3-anilino-5-pyrazolones.

6. The method of claim 1, wherein said coupling compound is 1-pentachlorophenyl-3-anilino-5-pyrazolones.

7. The method of claim 1, wherein said coupling compound contains 16 or more carbon atoms.

8. The method of claim 1, wherein said coupling compound is a compound represented by the following Formula (1):

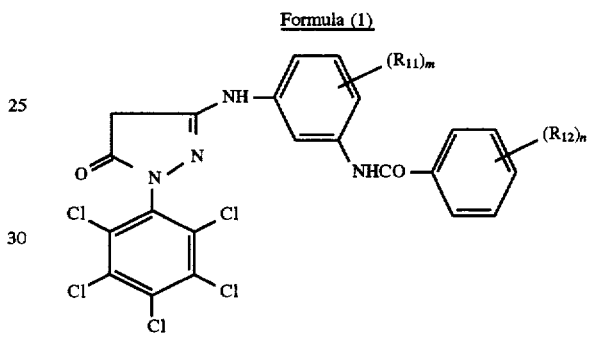

wherein $R^{11}$ and $R_{12}$ independently represent an alkyl, cycloalkyl, aryl, heterocyclic, alkylcarbonyl, alkylsulfonyl, arylcarbonyl, alkoxycarbonyl, aryloxycarbonyl, arylsulfonyl, alkylsulfinyl, arylsulfinyl, carbamoyl, sulfamoyl, cyano, amino, alkylamino, arylamino, arylcarbonylamino, arylaminocarbonyl, sulfonamide, amido, ureido, thioureido, alkoxy, aryloxy, alkylthio, arylthio, carboxy, sulfo or hydroxy group or a halogen atom; m represents an integer of 0 to 4; and n represents an integer of 1 to 5.

9. The method of claim 1, wherein said disulfide is a symmetric diaryldisulfide.

10. The method of claim 1, wherein said disulfide has an aryl group having a substituent at an ortho-position regarding S in the disulfide.

11. The method of claim 1, wherein said disulfide is a compound represented by the following Formula:

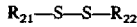

wherein at least one of $R_{21}$ and $R_{22}$ contains 12 or more carbon atoms.

12. The method of claim 1, wherein said disulfide is a compound represented by the following Formula (2):

Formula (2)

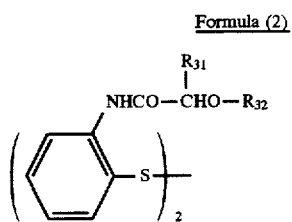

wherein $R_{31}$ represents an alkyl group; and $R_{32}$ represents an aryl group.

13. The method of claim 1, wherein s aid pKa of said base is 4 to 20.

14. The method of claim 1, wherein said thiol is 2-aminothiophenols.

15. The method of claim 1, wherein said second oxidizing agent is hydrogen peroxide.

16. The method of claim 1, wherein said reacting is carried out further in the presence of an amide solvent.

17. The method of claim 16, wherein said amide solvent is dimethylformamide.

18. The method of claim 1, wherein said second oxidizing agent is a hypohalogenite.

19. The method of claim 18, wherein said hypohalogenite is a hypochlorite.

20. The method of claim 1, wherein said base is carbonates or caustic alkalis.

21. The method of claim 1, wherein said reacting is carried out by adding said second oxidizing agent in such a manner that the addition amount of said second oxidizing agent does not exceed an amount necessary to oxidize a sulfide anion produced during the reaction to disulfide, until at least ⅔ of the coupler is consumed.

22. The method of claim 1, wherein said reaction mixture is further treated with carboxylic acids or sulfonic acids.

* * * * *